United States Patent [19]

Forward et al.

[11] Patent Number: 4,587,371
[45] Date of Patent: May 6, 1986

[54] HYDROCARBON CONVERSION OF SULFUR CONTAMINATED FEED STOCK

[75] Inventors: Cleve H. Forward; James R. Butler; William P. Licht, all of Big Spring, Tex.

[73] Assignee: Cosden Technology, Inc., Dallas, Tex.

[21] Appl. No.: 644,885

[22] Filed: Aug. 27, 1984

[51] Int. Cl.[4] .............................................. C07C 2/68
[52] U.S. Cl. ..................................................... 585/467
[58] Field of Search ........................................ 585/467

[56] References Cited

U.S. PATENT DOCUMENTS

| | | | |
|---|---|---|---|
| 4,016,218 | 4/1977 | Haaq et al. | 585/467 |
| 4,061,724 | 12/1977 | Grose et al. | 423/335 |
| 4,365,104 | 12/1982 | Kaeding | 585/467 |
| 4,387,260 | 6/1983 | Watson | 585/467 |
| 4,416,765 | 11/1983 | Chester et al. | 208/120 |

OTHER PUBLICATIONS

J. T. Baker Chemical Company Catalog (1961), p. 51.
Fyfe et al., *Nature*, vol. 296, pp. 530–533, Apr. 8, 1982.
Fyfe et al., *Chemistry Letters* 1983, pp. 1551–1554.
Thomas et al., *Chemistry Letters* 1983, pp. 1555–1556.

*Primary Examiner*—Curtis R. Davis
*Attorney, Agent, or Firm*—Richards, Harris, Medlock & Andrews

[57] ABSTRACT

A process for the alkylation of aromatic hydrocarbons in a reaction zone containing a crystalline silica polymorph silicalite catalyst. The feed stock to the reaction zone comprises an alkylating agent and an aromatic substrate contains sulfur in an amount, greater than 2 ppm, which heretofore has considered to be unacceptable to zeolite catalysts. A steam cofeed may also be applied to the reaction zone in an amount sufficient to reduce the deposition of coke on the catalyst due to the presence of sulfur. Sulfur may be present as a contaminant in the aromatic substrate or the alkylating agent.

7 Claims, 4 Drawing Figures

HYDROCARBON CONVERSION OF SULFUR CONTAMINATED FEED STOCK

TECHNICAL FIELD

This invention relates to the alkylation of aromatic hydrocarbons by processes employing silicalite catalysts and more particularly to such alkylation processes which are tolerant to sulfur containing feed stocks.

BACKGROUND ART

Aromatic conversion processes, and in particular alkylation of aromatic substrates, are involved in the production of a wide variety of petrochemical products. For example, alkyl substituted aromatics such as ethyl benzene and ethyl toluene are employed as intermediates which are converted to important styrene and vinyl toluene monomers useful in the production of a variety of styrene polymers. At present many alkylation processes include processing steps in which the aromatic substrates are contacted under alkylation conditions in the presence of catalyst materials. Both single and multiple catalyst bed processes are well known in the art.

Catalyst properties that are important in the conversion process include the selectivity of the catalysts to the desired product and the activity of the catalyst both initially, i.e., when the catalyst is fresh, and as a function of time. The selectivity of the catalyst is characterized as the concentration of the desired product in the total product, expressed as weight percent or mole percent, and the conversion activity of the catalyst is characterized as the amount of the desired product expressed as a mole percent of the stoichiometrically limiting reactant. Catalysts in hydrocarbon conversion processes are subject to being "poisoned" with use due to various factors such as coke accumulation on the catalyst, or the presence of catalyst poisons such as sulfur and other impurities in the feedstream.

Among the catalysts which may be employed in the alkylation of aromatic compounds are the shape-selective molecular sieves which include the zeolites. Zeolites are crystalline alumino-silicates which have ion exchange capacities. Thus, U.S. Pat. No. 4,016,218 to Haag et al discloses the alkylation of aromatic compounds by a process in which the aromatic charge stock and the olefinic alkylating agent are brought into contact with an alumino-silicate zeolite. The zeolite has a constraint index of one to twelve and more than 50% of the cationic sites on the catalyst are occupied by hydrogen ions. Specifically disclosed for use in the Haag et al process are the zeolites identified as ZSM-5, ZSM-11, ZSM-12, ZSM-35, ZSM-38. Another alkylation process employing zeolite catalysts is disclosed in U.S. Pat. No. 4,365,104 to Kaeding. In this case, the zeolite catalyst is treated with a sulfur based agent, preferably after prior treatment with phosphorus and magnesium compounds, in order to increase the para-selectivity of the catalyst. Kaeding discloses that the zeolite catalyst may be treated with a highly oxidized compound such as sulfur dioxide or a highly reduced compound such as hydrogen sulfide. The catalysts disclosed in Kaeding include those disclosed in the aforementioned Haag patent and in addition a "highly siliceous" zeolite identified as ZSM-48. This catalyst, while characterized as having a silica to alumina ratio of up to infinity, is disclosed as having an ion exchange capacity and thus appears to be a true zeolite rather than a silicalite of the type described below.

Crystalline silicalites are another class of molecular sieves useful as catalysts. The silicalites, while having topological configurations similar to those of the zeolites, do not include the tetrahedral alumina structure characteristic of zeolites and are not ion exchangers. Silicalites have also been employed to advantage in the alkylation of aromatic compounds. Thus, U.S. Pat. No. 4,387,260 to Watson et al discloses an aromatic alkylation procedure in which steam is fed to the catalytic reactor along with the aromatic feed stock and the alkylating agent. The steam functions to maintain the alkylation activity of the catalyst and to increase the selectivity of the process for desired alkyl aromatics.

Heretofore, the zeolite catalyst systems set forth in the prior art have not been disclosed as useful in the alkylation of aromatic feed stocks containing a significant quantity of sulfur as a contaminant. In fact, the commercial specifications for benzene, a common feedstock used in aromatic alkylation procedures, suggest that such catalysts are not sulfur tolerant. Thus, the specification Benzene-535 ASTM 2359-66T requires that the benzene be free of sulfur compounds such as $H_2S$ and $SO_2$ and contain no more than one part per million (PPM) thiophene. Other specifications require a maximum total sulfur concentration of 2 ppm. Similarly, the aforementioned patent to Kaeding, while disclosing that hydrogen sulfide or sulfur dioxide will increase the para selectivity of a ZSM-5 type zeolite catalyst, specifies that the catalyst be contacted with the treating agent prior to the alkylation process and then calcined prior to the alkylation process. The pretreatment preferably takes place in an anhydrous environment.

DISCLOSURE OF THE INVENTION

In accordance with the present invention, there is provided a process for the alkylation of aromatic hydrocarbons employing a feedstock containing sulfur in an amount heretofore considered to be unacceptable to zeolite catalysts. In carrying out the invention, an alkylating agent and an aromatic substrate are passed to a reaction zone containing a crystalline silica polymorph silicalite catalyst. The feedstream to the reaction zone contains sulfur in an amount greater than 2 ppm. Conversion conditions are maintained within said reaction zone to provide for the alkylation of the aromatic charge. In another application of the invention, the aromatic feed stock contains sulfur in an amount greater than 2 ppm up to about 20 ppm and in yet a further application of the invention the sulfur content of the feed stock is at least 6 ppm.

In another embodiment of the invention, steam is passed into the reaction zone and into contact with the catalyst along with the aromatic feedstock and the alkylating agent. The steam feed is sufficient to reduce deposition of coke on the catalyst due to the presence of sulfur. Preferably, the steam is passed into the reaction zone in an amount within the range of 7000–40,000 ppm based upon the aromatic feed.

DETAILED DESCRIPTION

Figure 3:
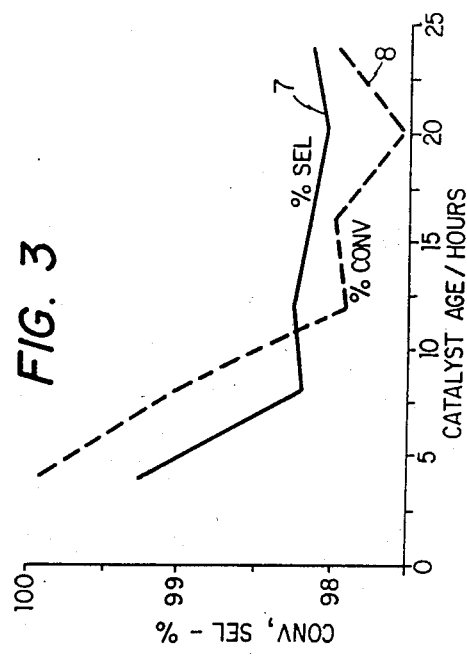
FIG. 3 is a graph of selectivity and activity as a function of catalyst age observed in experimental work carried out on a regenerated catalyst.

In carrying out the alkylation process in accordance with the present invention, the sulfur contaminated feedstock comprising the aromatic substrate and alkylating agent or agents is passed to a reaction zone containing a crystalline silica polymorph silicalite catalyst. Within this zone, the reactants are allowed to contact the catalyst under appropriate conditions of temperature, pressure and residence time for the desired alkylation process. Normally the inlet temperature to the reaction zone will be within the range of about 350°–500° C. and preferably within the range of about 400°–420° C. The normal operating is pressure within the range of about 10–25 bars. The aromatic substrate material normally will be passed through the reaction zone at a rate to provide a weight hourly space velocity (WHSV) within the range of 10–110. The feedstock may contain any aromatic compounds which are suitable for the production of alkyl aromatics. Thus the aromatic feed stock may contain mononuclear aromatics such as benzene, toluene, and ethyl benzene or polynuclear reactants such as naphthalene and the corresponding alkyl naphthalenes. The alkylating agents similarly may be of any suitable type normally employed in commercial alkylating processes. Suitable alkylating agents include olefins, aliphatic alcohols, and alkyl halides. As a practical matter, it will usually be preferred to employ olefins such as ethylene, propylene or butene as the alkylating agents.

The alkylation process can be carried out using appropriate processing equipment including a reactor vessel which defines the reaction zone and contains the silicalite catalyst. The silicalite catalyst may be arranged in either a single bed or in multiple beds within the reaction zone. The reactants such as benzene and ethylene can be admixed and preheated prior to introduction into the reaction zone or these reactants may be applied separately to the reaction zone. As described in greater detail hereinafter, steam can be mixed with the reactants prior to introduction into the reaction zone. After maintaining the charge stock within the reaction zone for the desired residence time, the converted alkyl aromatic effluent passes out of the reaction vessel and the desired products may be collected by a standard recovery technique such as condensation.

The relative amounts of aromatic substrates and alkylating agents applied to the reaction zone will vary depending upon the desired reaction product. In most cases, it will be preferred to enhance monoalkylation reactions and depress polyalkylation and, thus, the aromatic feed stock will be employed in a substantial molar excess relative to the alklyating agent. In the monoalkylation of benzene using a sulfur contaminated feed stock and ethylene is described hereinafter, it will be preferred to provide a molar ratio of benzene to ethylene of about 8. As noted previously, the reaction products may also be influenced by the residence time, as determined by the weight hour space velocity, pressure and temperature.

The catalyst material employed in the present invention is a true crystalline silica material as opposed to a zeolite material, which, by definition, is a silicate of aluminum and either sodium or calcium, or both, which demonstrates ion exchange capacity. The crystalline silica materials used as catalysts in the present invention are silica polymorphs whose structures have been designated as "silicalite". These materials, in contrast to aluminosilicate zeolites, demonstrate no appreciable ion exchange properties since $AlO_4^-$ tetrahedra do not comprise a portion of the crystalline silica framework. Aluminum may be present in these silicalite catalyst materials. However, its presence is a result of impurities in the silica source used to prepare the material and silicalite containing such alumina or other metal oxide impurities can in no sense be considered to be a metalosilicate. Further description and methods for preparing silicalite type catalysts are set forth in U.S. Pat. No. 4,061,724 to Grose et al, the entire disclosure of which is incorporated herein by reference.

In addition to the physical and chemical distinctions between crystalline silica polymorph silicalite type catalysts and aluminosilicate zeolites, several functional distinctions are also apparent as regards the use of these materials as hydrocarbon conversion catalysts. For example when ZSM-5 type aluminosilicate zeolites are employed in alkylation reactions, they are reported to rapidly lose catalytic activity in the presence of even minor amounts of water. As noted in the aforementioned patent to Watson, et al., the crystalline silica polymorph silicalite materials employed in the present invention are useful as alkylation catalysts even in the presence of steam. In fact, in most instances, performance of the process can be enhanced through the use of a steam co-feed.

Another important distinction which is employed to advantage in the present invention, lies in the tolerance of the silicalite catalyst to sulfur concentrations heretofore thought to be unacceptable at the conversion conditions employed in the alklyation of aromatic compounds. As noted previously, the commercial specifications for the alkylation of aromatics over zeolite catalysts are very strict, permitting no more than two parts per million sulfur. Also, as disclosed in the aforementioned patent to Kaeding, while inorganic sulfur values are described as increasing the para selectivity of zeolite catalysts, the catalysts are treated prior to the alkylation process rather than under the conditions prevailing in the course of the alklyation procedure.

In contrast to the low sulfur tolerance of the zeolite catalysts heretofore employed in the alkylation of aromatic hydrocarbons, the silicalite catalyst employed in the present invention permit the use of aromatic feed stocks having sulfur contamination levels several times greater than those heretofore considered to be acceptable. This offers an important commercial advantage since it increases the availability of aromatic feed stocks for the conversion process and enables the use of less expensive feed stocks. Specifically, the aromatic feed stock contains sulfur in an amount greater than 2 ppm. Experimental work described in greater detail hereinafter indicates that a sulfur contamination up to 7 parts per million is readily tolerated and a preferred application of the invention is in the alkylation of aromatic feed stocks containing sulfur in an amount greater than 2 ppm no more than 7 ppm. Further, while greater sulfur contamination levels have not been investigated experimentally, it is believed that feed stocks containing sulfur in amounts well in excess of 7 ppm can be employed in accordance with the present invention with better results than are possible through the use of zeolite catalyst at these higher sulfur contamination levels.

In addition to or instead of sulfur contamination in the aromatic feedstock, the feedstream to the reaction zone may contain sulfur as a result of sulfur contamination of the alkylating agent. Thus, a refining stream which contains a desired olefinic alkylating agent such as ethylene, usually in the presence of other hydrocarbons, may be employed as the alkylating agent not withstanding that it contains a substantial sulfur concentration. Such refinery streams are sometimes available and suitable as alkylating agents other than their heretofore unacceptably high sulfur contents. Sulfur may be present in amounts up to 100 ppm or more, resulting in a sulfur contamination in the feedstream when the alkylating agent is mixed with the aromatic charge either before application to the reaction zone or within the reaction zone, greater than 2 ppm and ranging up to about 20 ppm. This is considered to be well within the tolerance level of the silicalite catalyst.

A further advantage of the present invention resides in the fact that a steam cofeed may be employed similarly as in the case of the aforementioned Watson, et al. patent, not withstanding that the feedstream to the reaction zone contains sulfur in amounts above what has been heretofore considered to be acceptable. In fact, it is believed that an effective amount of steam in the cofeed actually reduces coking due to sulfur and therefore increases the useful life of the catalyst.

A preferred catalyst for use in the alkylation of an aromatic substrate in accordance with the present invention is a silicalite having a crystallite size of less than 8 microns and a ratio of silica to alumina in the tetrahedra molecular sieve network of at least about 200. Typical processes include monoalkylation procedures to produce ethylbenzene and ethyltoluene as produced from benzene and toluene feedstreams, respectively. In experimental work carried out respecting the invention, a catalyst meeting the specifications described immediately above was employed in the monoalkylation of benzene with ethylene to produce ethylbenzene. In a first test procedure, a mixture of benzene, ethylene and steam was applied to a reaction zone containing the silicate catalyst and operated under a pressure of about 21 bars (300 psig). The inlet temperature was maintained at a value of 420° C. and the premixed feed stream was applied at a rate to supply benzene at a WHSV of 110. The molar ratio of benzene to ethylene was 8/1 and the steam was present in a concentration of 40,000 ppm of the benzene. The benzene feed stock contained mercaptan sulfur in an amount of 6.4 ppm.

Figure 1:
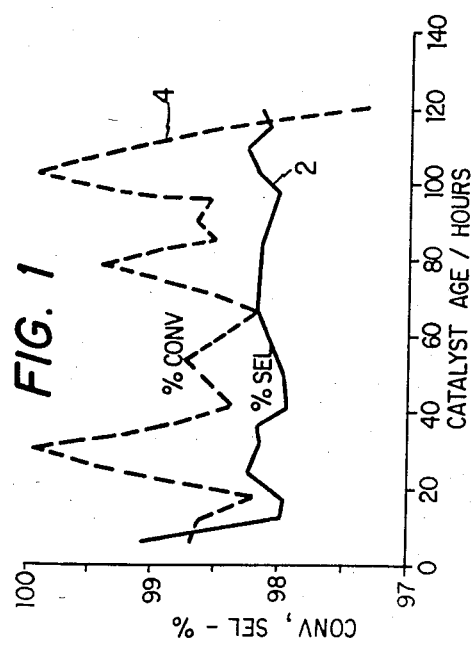
FIG. 1 is a graph of catalyst activity and selectivity as a function of catalyst age as observed during experimental work carried out relative to the invention.

Two runs were carried out following the above protocol. One employing fresh catalyst and another employing regenerated catalyst. The first run was carried out over a period of 120 hours. The results of this run in terms of the catalyst conversion activity and selectivity are set forth in FIG. 1. as shown in FIG. 1, curves 2 and 4 are graphs of selectivity and conversion, respectively, expressed as percent on the ordinate versus the catalyst age in hours on the abscissa. As shown in FIG. 1, the conversion factor (moles of ethylbenzene divided by moles of ethylene fed to the reactor) remained above 98% throughout most of the run and showed a slight tendency to deteriorate at the end of the test period. The selectivity factor (the quotient of the weight of ethylbenzene divided by the total product weight expressed as a percent) remained above 98% throughout most of the test period and showed no tendency to deteriorate with age. Throughout the test period the average conversion factor was 98.8% and the average selectivity was 98.2%.

Figure 2:
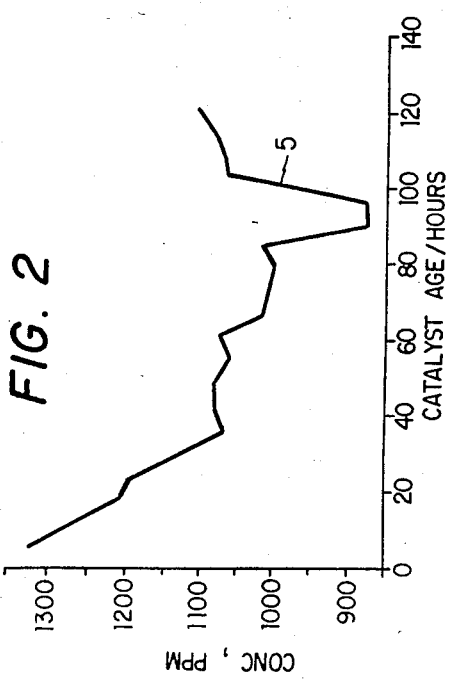
FIG. 2 is a graph illustrating the concentration of xylenes in the product as observed during the experimental work depicted in FIG. 1.

In FIG. 2, curve 5 is a graph of the xylene concentration expressed as parts per million relative to ethylbenzene plotted on the ordinate versus the catalyst age in hours plotted on the abscissa. The average xylene concentration over the test period was about 1075 ppm and showed only a slight tendency to increase toward the end of the test period. The total diethylbenzene in the product remained fairly constant over the test period averaging about 5.2% relative to monoethylbenzene.

At the conclusion of the first run the catalyst was regenerated in accordance with the following general procedure. First, the catalyst material is heated to 480° C. in the presence of nitrogen gas. After three hours of this treatment, steam is introduced at the rate of 28 WHSV. After 30 minutes, nitrogen is cut back to 12 WHSV. After 30 minutes, nitrogen is cut back to 12 WHSV and steam to 5 WHSV. At the end of 10 hours, steam is raised back to a level of 28 WHSV, nitrogen to 24 WHSV and air flow is introduced at 0.5 WHSV. Thereafter, the steam and nitrogen are slowly eliminated from the system and air flow increased stepwise over a period of three hours. Total regeneration time is about 18 hours.

Figure 4:
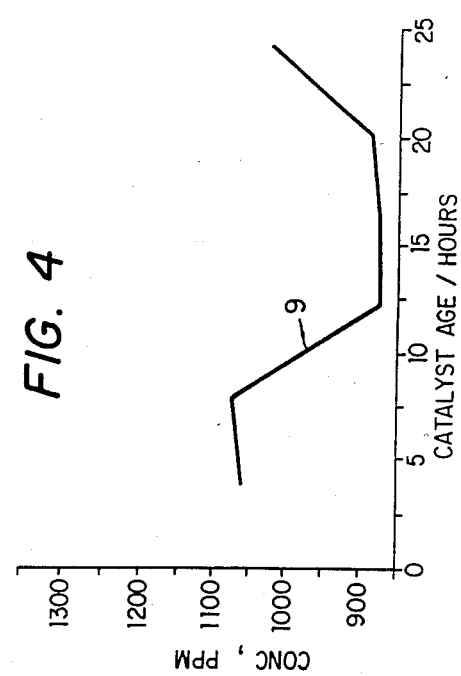
FIG. 4 is a graph illustrating the concentration of product xylenes as a function of the catalyst age for the experimental work depicted in FIG. 3.

After the regeneration process was completed, run number 2 was instituted employing the same protocol as before but with a test period of only 24 hours. The results of this test are depicted graphically in FIGS. 3 and 4. Curves 7 and 8 in FIG. 3 are graphs of selectivity and conversion activity, respectively, and curve 9 in FIG. 4 is a graph of xylene concentration all plotted as a function of catalyst age in hours on the abscissa. As shown, the conversion activity and selectivity after regeneration were very nearly the same as for the fresh catalyst. Xylene production also remained low and averaged about 964 ppm relative to ethylbenzene over the life of the test. Total diethylbenzene relative to monoethylbenzene remained relatively constant at about 5.5%.

From a consideration of the foregoing experimental work, it will be recognized that utilization of the silicalite catalyst in accordance with the present invention permits the use of aromatic feed stocks having substantially greater sulfur contamination levels than have herefore been considered acceptable. In addition, the catalyst retained a high activity over a substantial period of time and was susceptible to regeneration notwithstanding the relatively high concentration of sulfur contaminants.

Having described specific embodiments of the present invention, it will be understood that modifications thereof may be suggested to those skilled in the art, and it is intended to cover all such modifications as fall within the scope of the appended claims.

We claim:

1. In the alkylation of aromatic hydrocarbons the method comprising passing a feedstream of an alkylating agent and an aromatic substrate and containing sulfur in an amount greater than two ppm to a reaction zone containing a crystalline silica polymorph silicalite catalyst under conditions providing for the alkylation of said aromatic substrate.

2. The method of claim 1 wherein said feedstream contains sulfur in an amount of at least 6 ppm.

3. The method of claim 1 wherein said feedstream contains sulfur in an amount greater than two ppm and no greater than seven ppm.

4. The method of claim 1 wherein said feedstream contains sulfur in an amount greater than two ppm and no greater than 20 ppm.

5. The method of claim 1 further comprising the step of passing steam into said reaction zone and into contact with said catalyst in an amount sufficient to reduce the deposition of coke on said catalyst due to the presence of sulfur.

6. The method of claim 5 wherein said steam is passed into said reaction zone in an amount of at least 7000 ppm based upon said aromatic substrate.

7. The method of claim 5 wherein said aromatic substrate comprises benzene and said alkylating agent comprises ethylene and the molar ratio of benzene to ethylene is about 8.

* * * * *